United States Patent
Schweitzer et al.

(10) Patent No.: US 8,920,460 B2
(45) Date of Patent: Dec. 30, 2014

(54) SURGICAL INSTRUMENT

(75) Inventors: Tom Schweitzer, Tuttlingen (DE); Rupert Mayenberger, Rielasingen (DE)

(73) Assignee: Aesculap AG, Tuttlingen (DE)

( * ) Notice: Subject to any disclaimer, the term of this patent is extended or adjusted under 35 U.S.C. 154(b) by 518 days.

(21) Appl. No.: 12/925,251

(22) Filed: Oct. 14, 2010

(65) Prior Publication Data

US 2011/0106144 A1 May 5, 2011

(30) Foreign Application Priority Data

Oct. 15, 2009 (DE) .......................... 10 2009 045 749

(51) Int. Cl.
 *A61B 17/00* (2006.01)
 *A61B 17/29* (2006.01)
 *A61B 18/14* (2006.01)

(52) U.S. Cl.
 CPC ............. *A61B 17/29* (2013.01); *A61B 18/1445* (2013.01); *A61B 2017/00353* (2013.01); *A61B 2017/294* (2013.01); *A61B 2017/2938* (2013.01); *A61B 2017/2936* (2013.01)
 USPC ........................................................ 606/205

(58) Field of Classification Search
 CPC ........... A61B 17/28; A61B 2017/2931; A61B 2017/2938; A61B 2017/294
 USPC ..................... 606/51–52, 167, 170, 174, 183, 606/205–208, 144, 148, 139; 227/175.1, 227/182.1; 600/104, 562; 81/311, 314
 See application file for complete search history.

(56) References Cited

U.S. PATENT DOCUMENTS

| | | | | |
|---|---|---|---|---|
| 4,128,099 A | * | 12/1978 | Bauer | 606/52 |
| 5,314,424 A | * | 5/1994 | Nicholas | 606/41 |
| 5,425,743 A | * | 6/1995 | Nicholas | 606/208 |
| 5,620,415 A | * | 4/1997 | Lucey et al. | 604/22 |
| 5,797,939 A | * | 8/1998 | Yoon | 606/167 |
| 5,810,864 A | * | 9/1998 | Schaller | 606/170 |
| 5,893,875 A | * | 4/1999 | O'Connor et al. | 606/205 |
| 6,083,150 A | * | 7/2000 | Aznoian et al. | 600/564 |
| 6,358,268 B1 | | 3/2002 | Hunt et al. | |
| 6,506,208 B2 | * | 1/2003 | Hunt et al. | 606/205 |
| 7,875,028 B2 | * | 1/2011 | Christian et al. | 606/51 |
| 2005/0209596 A1 | * | 9/2005 | Daniels et al. | 606/83 |
| 2006/0184161 A1 | * | 8/2006 | Maahs et al. | 606/2 |
| 2011/0087267 A1 | * | 4/2011 | Spivey et al. | 606/205 |
| 2012/0078291 A1 | * | 3/2012 | Nobis et al. | 606/206 |

FOREIGN PATENT DOCUMENTS

DE 10 2007 023 960 12/2008

* cited by examiner

*Primary Examiner* — Katherine Dowe
*Assistant Examiner* — Amy Shipley
(74) *Attorney, Agent, or Firm* — Lipsitz & McAllister, LLC

(57) ABSTRACT

In order to provide a surgical instrument which is particularly simple to manipulate and enables force to be transmitted particularly directly to at least two tool elements wherein the surgical instrument comprises said at least two tool elements which are movable relative to one another and are arranged at a distal end of a guide device of a surgical instrument, and also comprises a force transmission device for transferring an actuating force from a proximal end of the force transmission device to a distal end of the force transmission device for the purposes of moving at least one of the at least two tool elements relative to the guide device, it is proposed that the surgical instrument should comprise a coupling device for selectively coupling the force transmission device directly or indirectly to at least one of the at least two tool elements.

23 Claims, 11 Drawing Sheets

US 8,920,460 B2

SURGICAL INSTRUMENT

CROSS-REFERENCE TO RELATED APPLICATIONS

Figure 1:
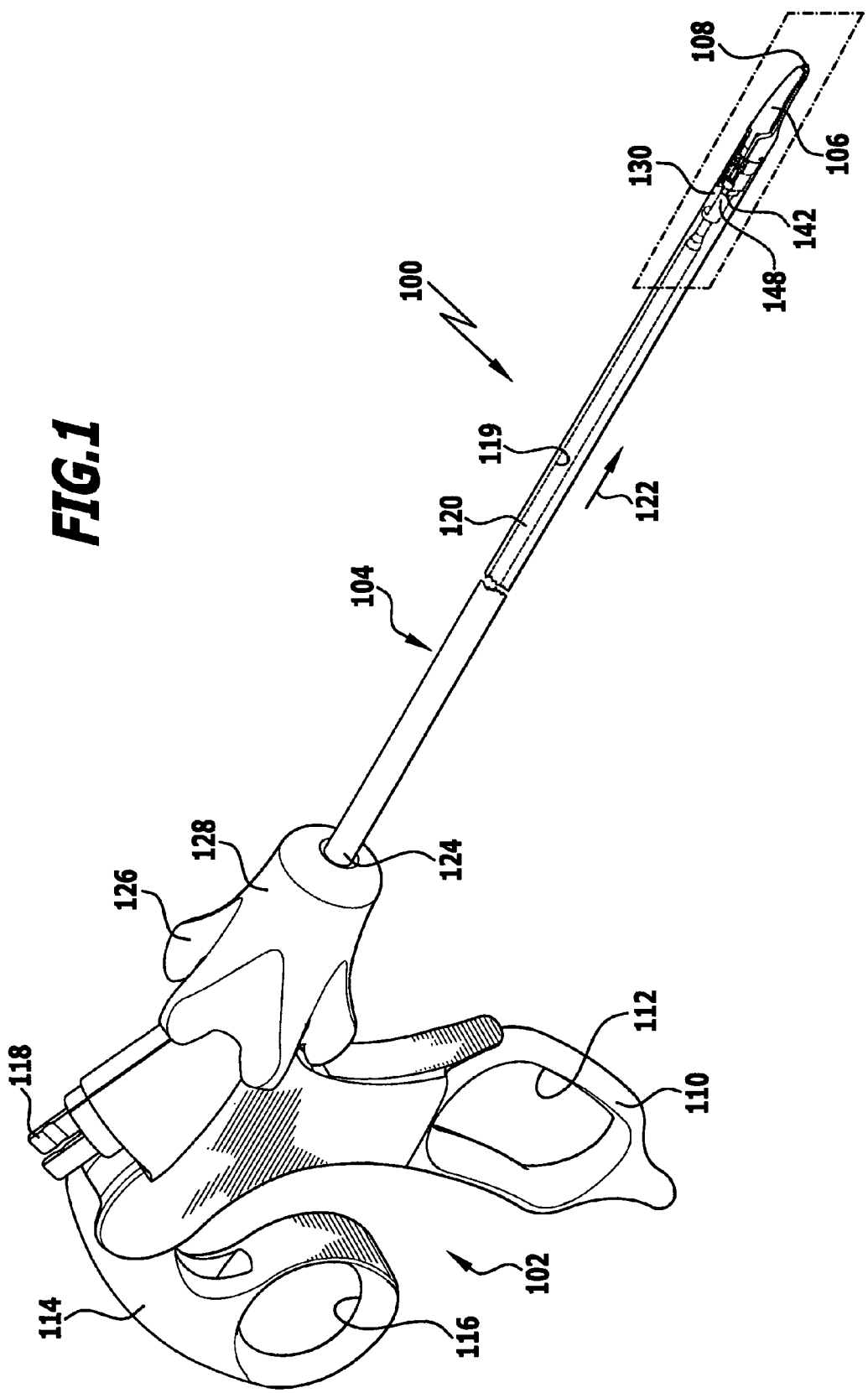

The present disclosure relates to the subject matter disclosed in German patent application number 10 2009 045 749.6, filed Oct. 15, 2009, which is incorporated by reference herein in its entirety and for all purposes.

FIELD OF THE INVENTION

The present invention relates to surgical instruments in general, and in particular to a surgical instrument which comprises at least two tool elements which are movable relative to each other and are arranged at a distal end of a guide device of the surgical instrument, and a force transmission device for transferring an actuating force from a proximal end of the force transmission device to a distal end of the force transmission device for the purposes of moving at least one of the at least two tool elements relative to the guide device.

BACKGROUND OF THE INVENTION

Surgical instruments of this type are known from the state of the art. In particular, two force transmission devices are used for example, for transferring an actuating force to two tool elements, wherein a force transmission device is associated with each tool element. In particular in the case of surgical instruments in the form of tubular shaft instruments for example, the two force transmission devices for transferring an actuating force to the tool elements are, for example, then fed side-by-side through the tubular shaft and they must be of particularly thin construction due to the preferably small diameter of the tubular shaft. Now if an actuating force is exerted on the tool element by means of the force transmission device, then it can happen in the case of the surgical instruments known from the state of the art that a force transmission device will be deformed and thus make it more difficult to properly transmit the desired force to the tool element.

Consequently, it would be desirable to provide a surgical instrument which is particularly easy to manipulate and which enables force to be transmitted directly to at least two tool elements that are movable relative to one another.

SUMMARY OF THE INVENTION

In a first aspect of the invention, a surgical instrument comprises at least two tool elements that are movable relative to one another, a guide device, a force transmission device and a coupling device. The force transmission device is configured for transferring an actuating force for the purposes of moving at least one of the at least two tool elements relative to the guide device. The coupling device is configured for selectively coupling the force transmission device directly or indirectly to at least one of the at least two tool elements.

BRIEF DESCRIPTION OF THE DRAWING FIGURES

Figure 2:
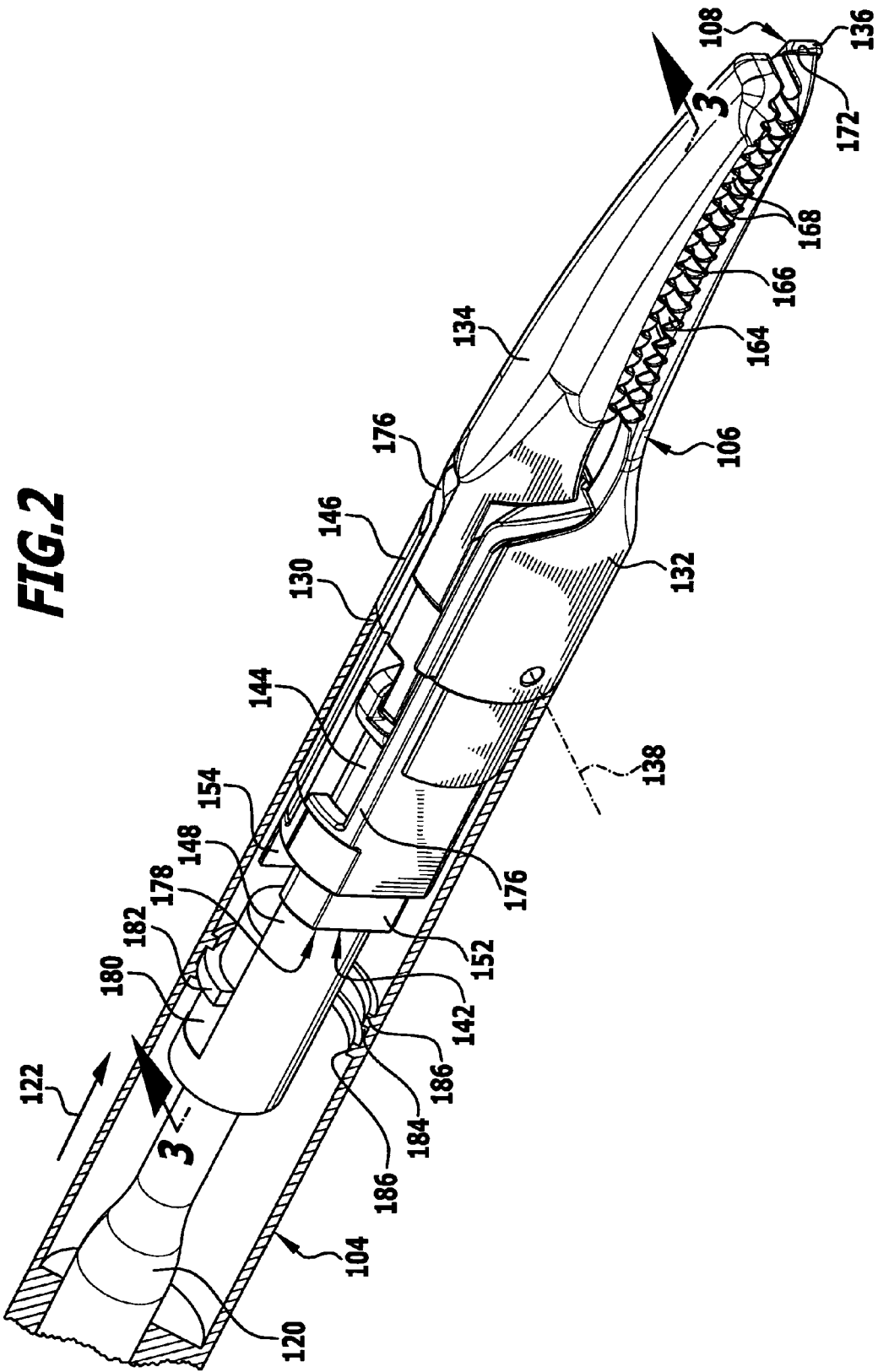
Figure 3:
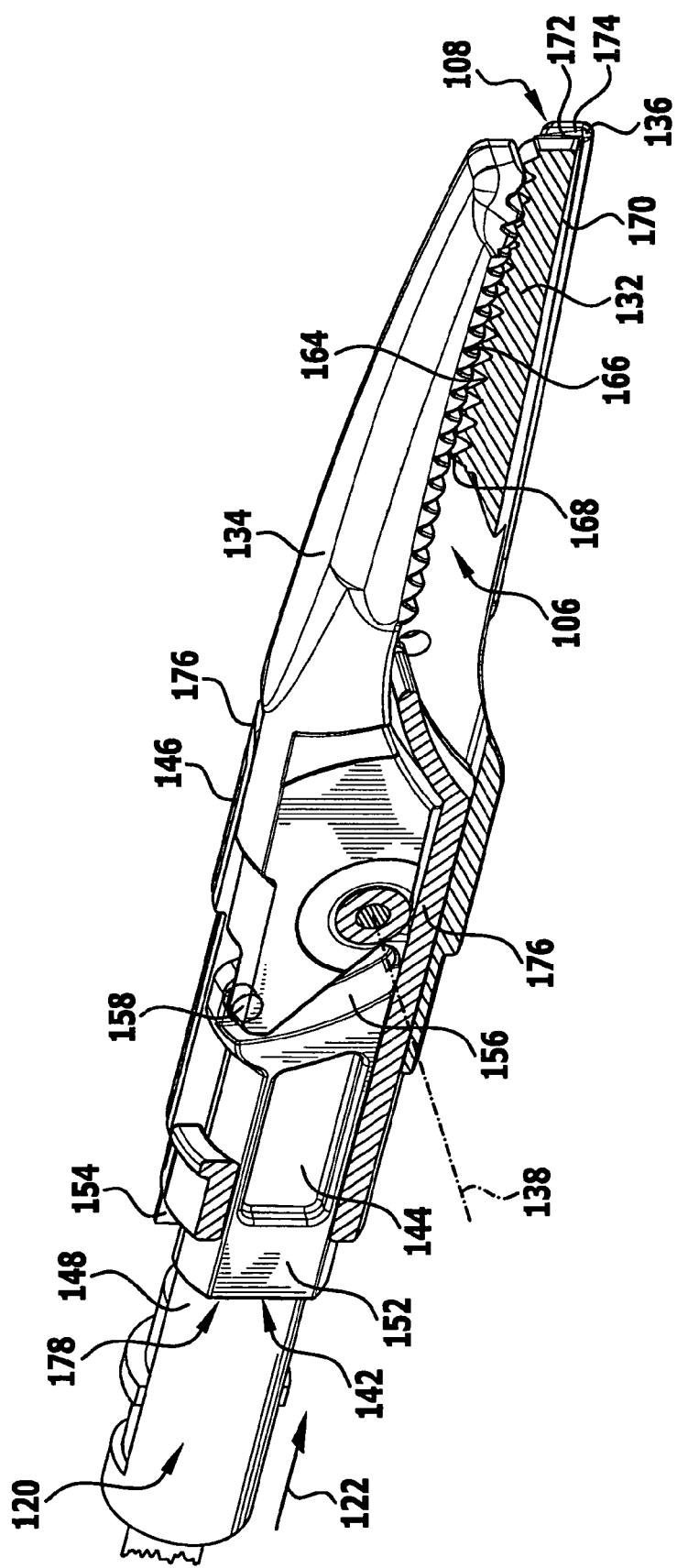
Figure 4:
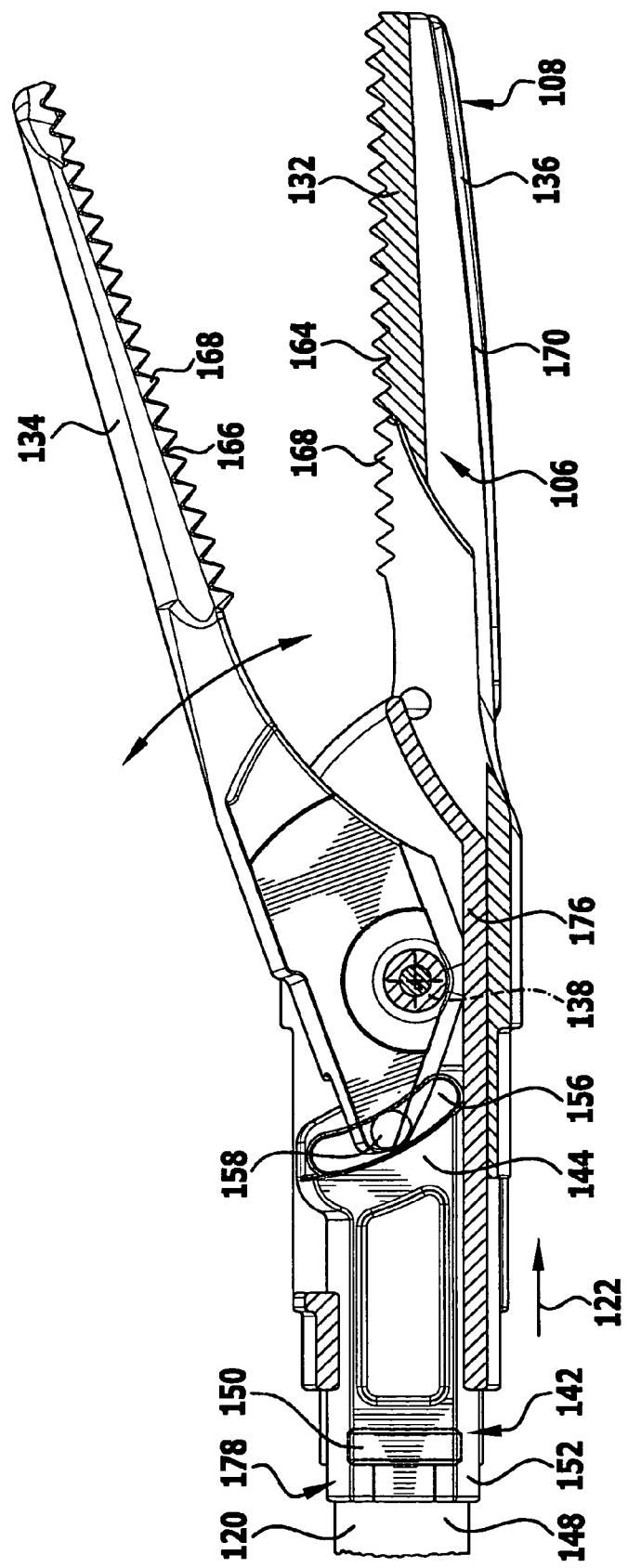
Figure 5:
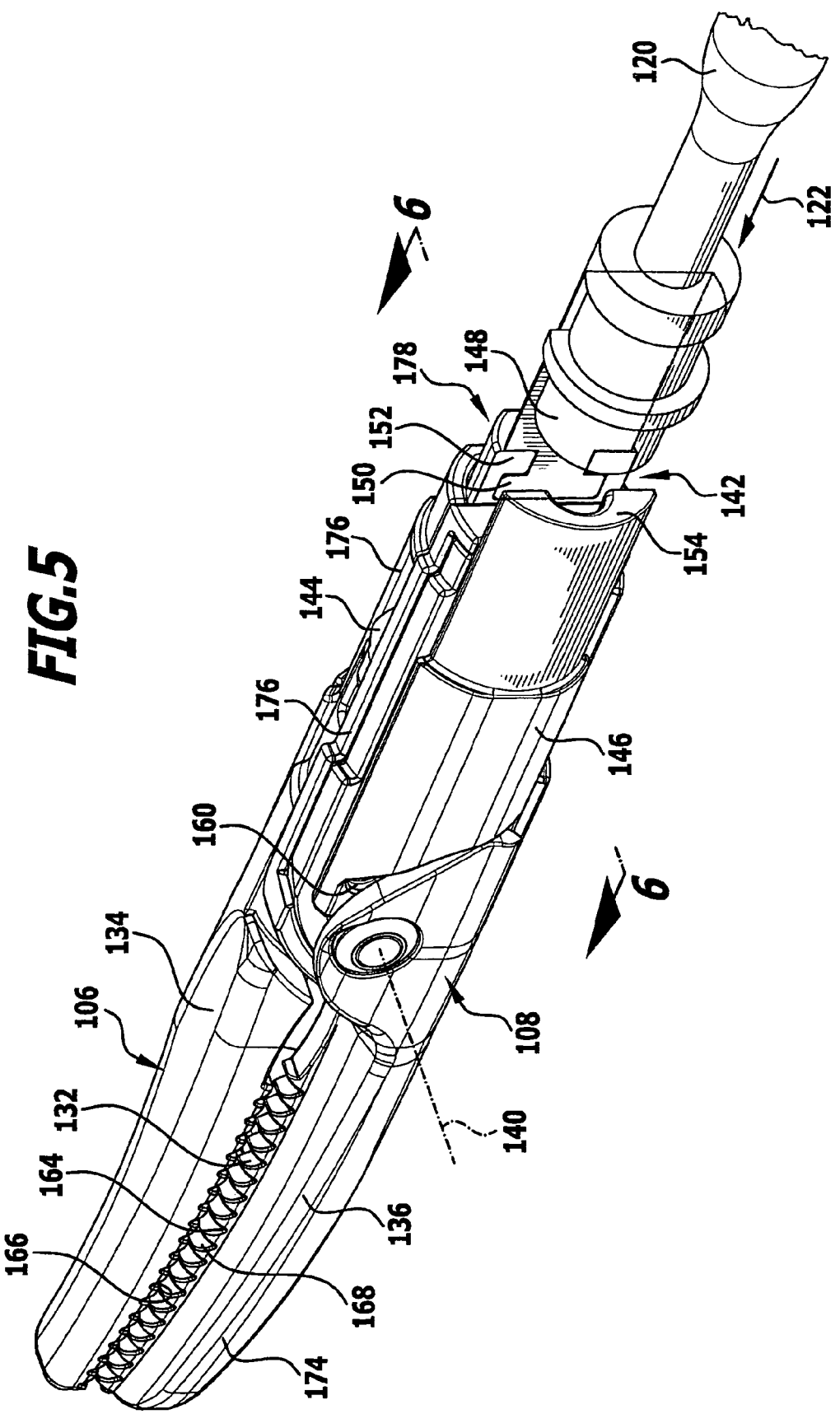
Figure 6:
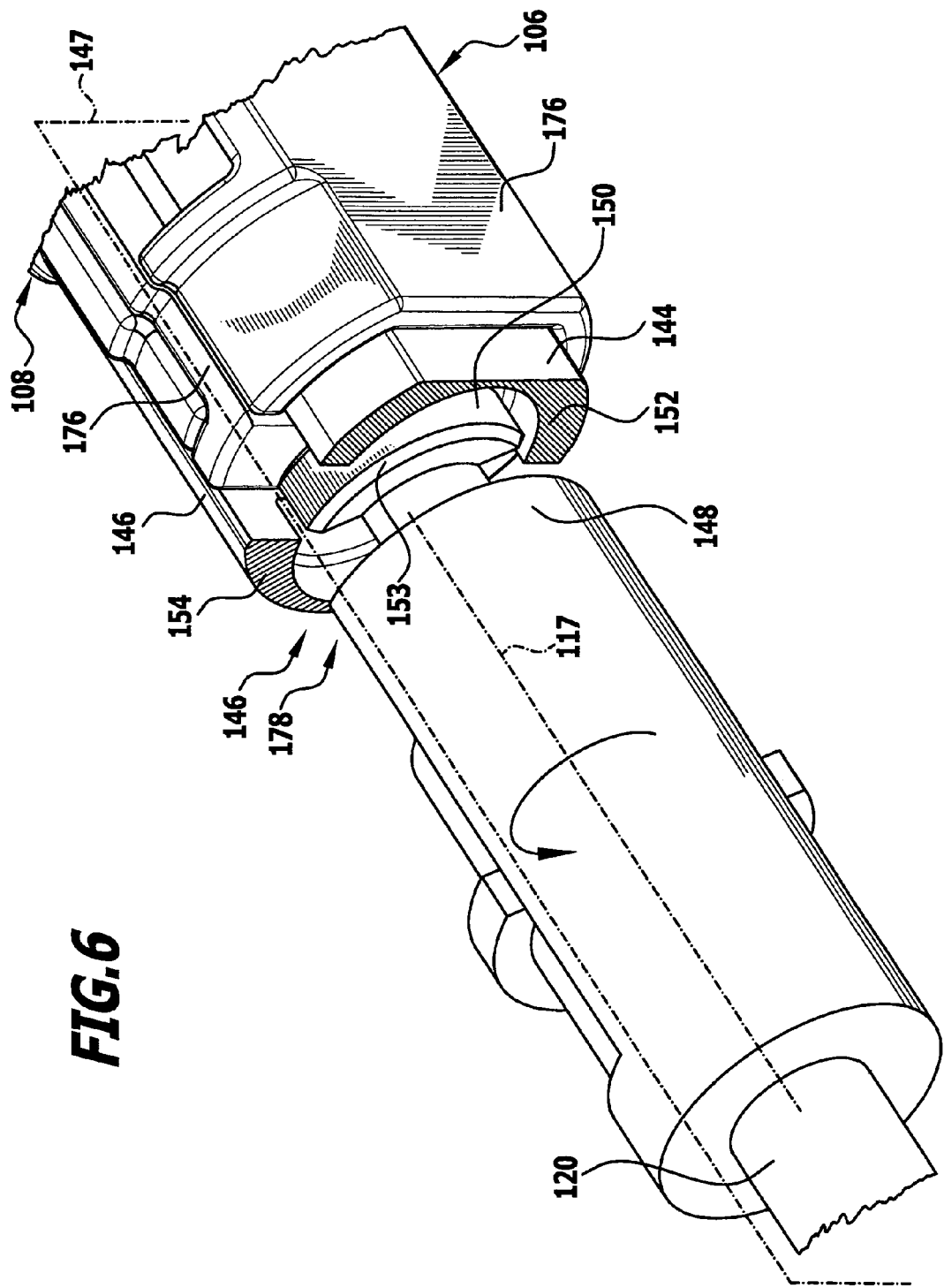
Figure 7:
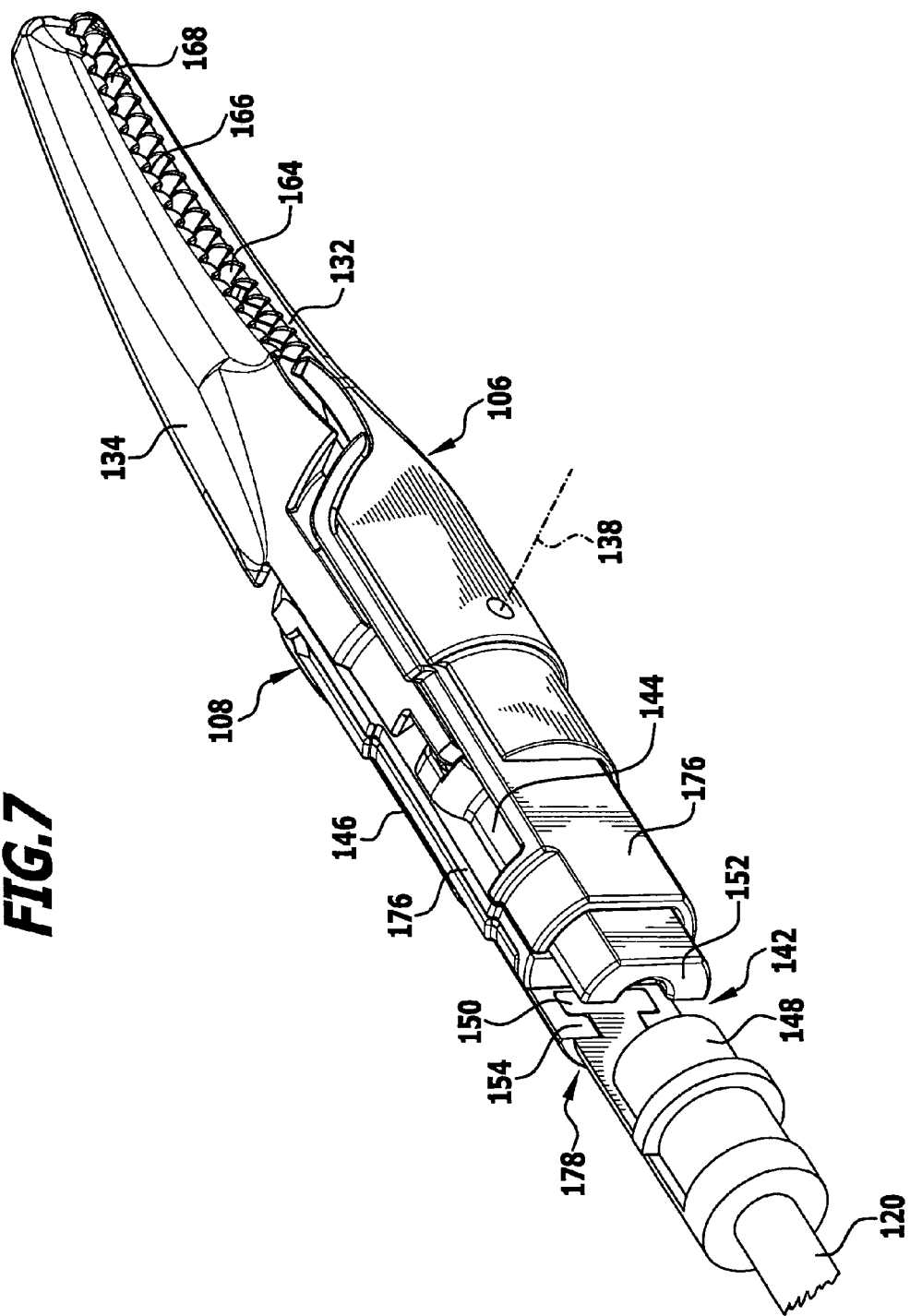
Figure 8:
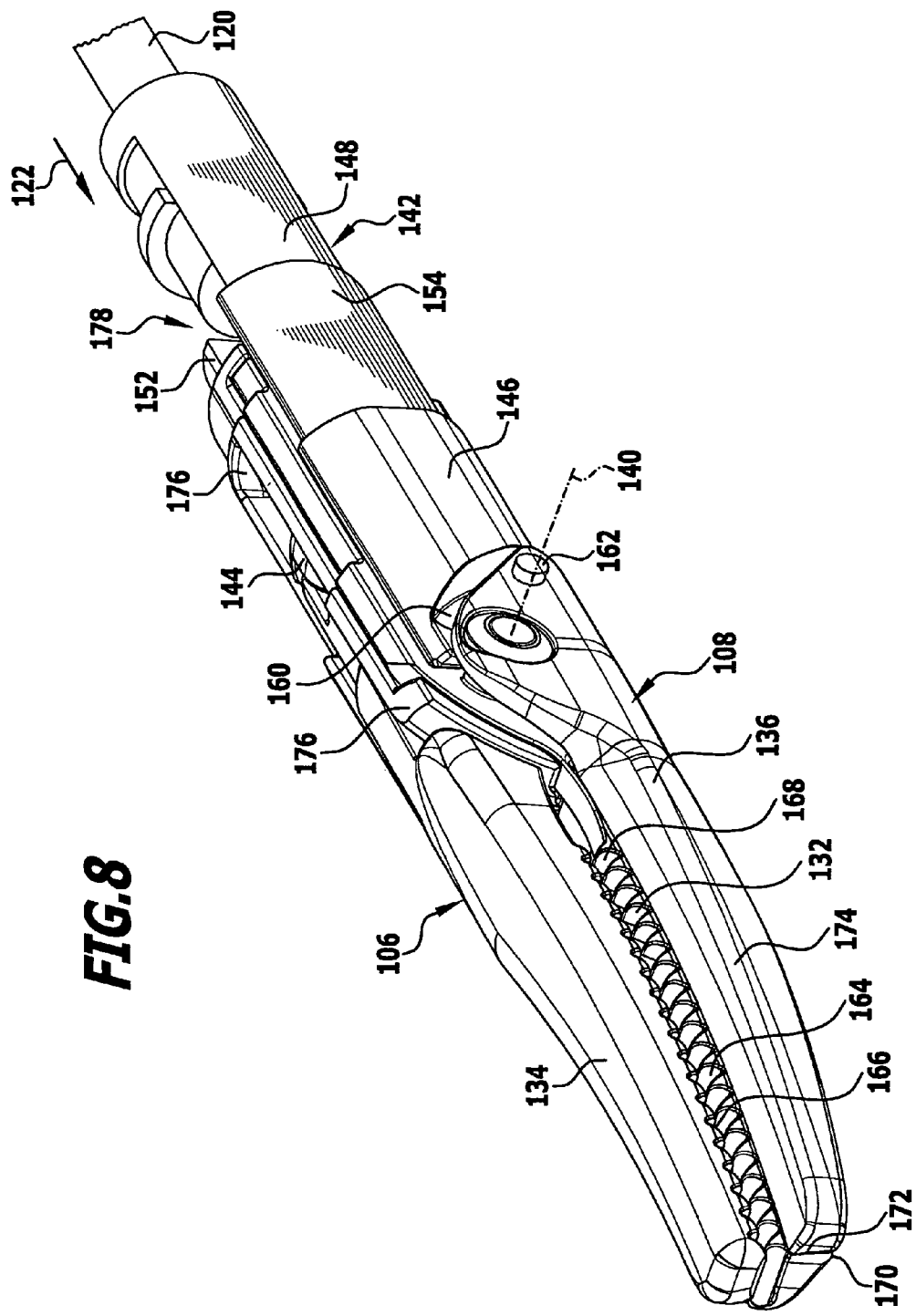
Figure 9:
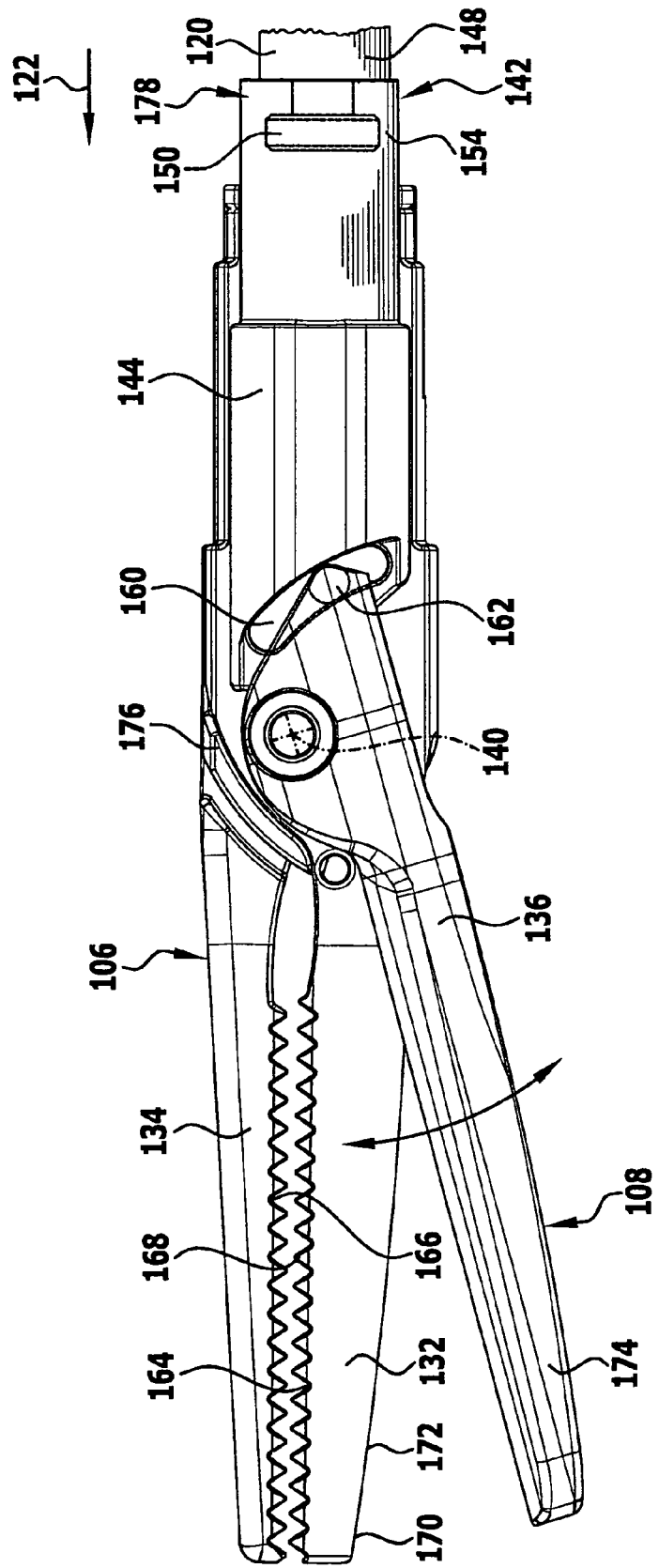
Figure 10:
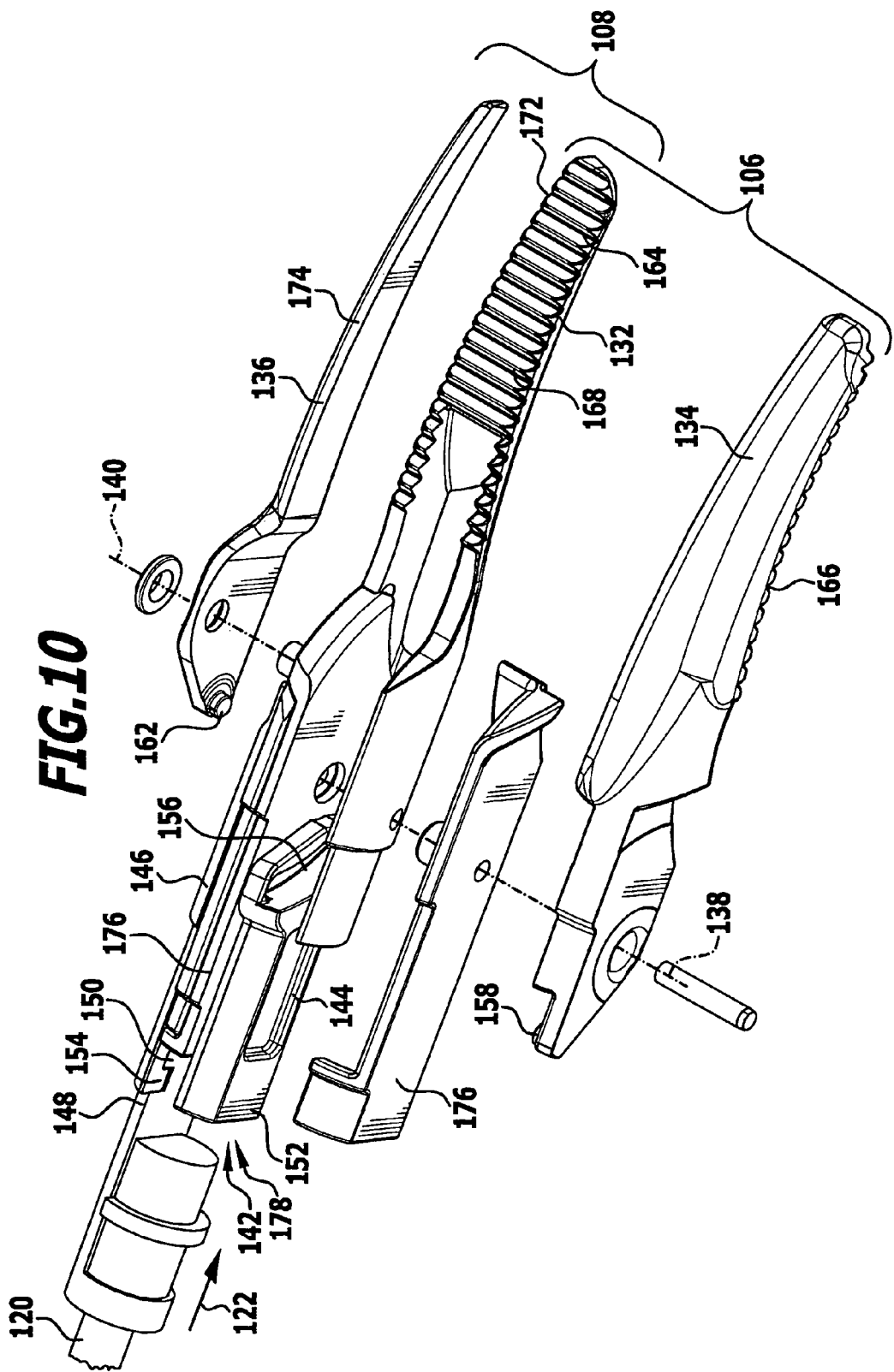
Figure 11:
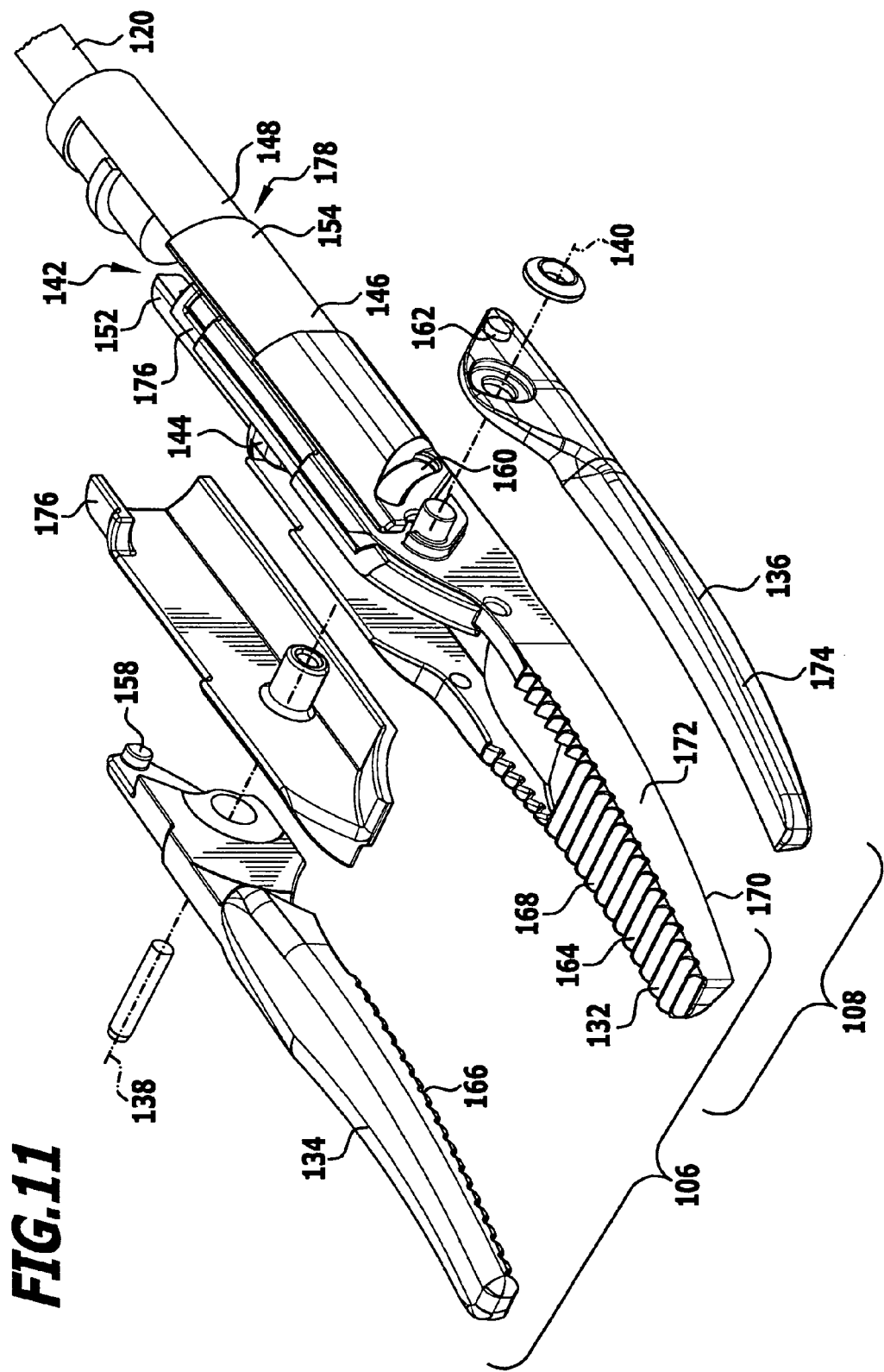

The foregoing summary and the following description may be better understood in conjunction with the drawing Figures, of which:

FIG. 1: is a schematic perspective illustration of a surgical instrument;

FIG. 2: is a schematic perspective illustration of a distal end of a guide device of the surgical instrument, including a force transmission device that is guided in the guide device, tool elements arranged at the distal end of the guide device and a coupling device for coupling the force transmission device to the tool elements;

FIG. 3: is a schematic perspective illustration of a horizontal section through the force transmission device, the coupling device and the tool elements from FIG. 2 along the line 3-3 in FIG. 2;

FIG. 4: is a schematic side view of the force transmission device, the coupling device and two tool elements, wherein a first movable tool element is arranged in an open position;

FIG. 5: is a schematic perspective illustration of the coupling device and the tool elements, with a view of a second movable tool element;

FIG. 6: is an enlarged illustration of a distal end of the force transmission device and of the end of the coupling device facing the force transmission device, wherein two coupling elements of the coupling device are cut in the horizontal direction along the line 6-6 in FIG. 5 and the force transmission device is arranged in an intermediate position between two coupling positions;

FIG. 7: is a schematic perspective illustration of the force transmission device, the coupling device and the tool elements, wherein the coupling device is coupled to a second coupling element associated with the second movable tool;

FIG. 8: is a schematic perspective illustration of the force transmission device, the coupling device and the tool elements with a view of the second movable tool element, wherein the force transmission device is coupled to the coupling element which is associated with the second movable tool element;

FIG. 9: is a schematic side view of the force transmission device, the coupling device and the tool elements with a view of the second movable tool element which is arranged in an open position;

FIG. 10: is a first exploded illustration of the tool elements and the coupling device; and FIG. 11: is a second exploded illustration of the tool elements and the coupling device.

DETAILED DESCRIPTION OF PREFERRED EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical instrument which comprises at least two tool elements that are movable relative to one another, a guide device, a force transmission device and a coupling device. The tool elements are preferably arranged at a distal end of the guide device. The force transmission device is configured for transferring an actuating force, preferably from a proximal end of the force transmission device to a distal end of the force transmission device, for the purposes of moving at least one of the at least two tool elements relative to the guide device. The coupling device is configured for selectively coupling the force transmission device directly or indirectly to at least one of the at least two tool elements.

Due to the fact that the surgical instrument comprises a coupling device for selectively coupling the force transmission device to at least one of the at least two tool elements, a single force transmission device can be provided in the surgical instrument. Consequently, it is not necessary to provide a separate force transmission device for each of the tool elements of the surgical instrument.

Furthermore, due to the fact that the surgical instrument comprises a coupling device for selectively coupling the force transmission device directly or indirectly to one of the at least two tool elements, the force transmission device can be of robust construction since additional space for an additional force transmission device on the surgical instrument is not needed. In this way, an actuating force for moving at least one of the at least two tool elements relative to the guide device can be transferred from a proximal end of the force transmission device to a distal end of the force transmission device by means of the force transmission device, whereby deformation of the force transmission device will not occur or will only occur to a slight extent even if a larger actuating force is used. In this way, it is possible for the surgical instrument to be manipulated in a particularly simple manner and for force to be transmitted to the at least two tool elements of the surgical instrument in a particularly direct manner.

In one embodiment of the invention, provision is made for the force transmission device to be arranged at least partly within the guide device.

As an alternative thereto, provision may be made for the guide device to be arranged at least partly within the force transmission device.

It is expedient for the force transmission device to be moveable from a first coupling position in which the force transmission device is coupled to a first tool element of the surgical instrument, into a second coupling position in which the force transmission device is coupled to a second tool element of the surgical instrument. In this way, it is particularly easy to switch between the first coupling position for the actuation of the first tool element and the second coupling position for the actuation of the second tool element. Hereby, the force transmission device is preferably coupled exclusively to a respective one of the two tool elements, whilst the other tool element is fixed expediently in a resting position.

The force transmission device is preferably mounted on the guide device in rotatable manner. Such a mounting arrangement is particularly advantageous when the coupling device of the surgical instrument is operable by rotating the force transmission device relative to the guide device.

Furthermore, the force transmission device is preferably formed to be at least partially electrically conductive. In this way, the force transmission device can be used as a current conducting device for conveying an electric current to at least one of the at least two tool elements of the surgical instrument.

In a preferred embodiment of the invention, provision may be made for the force transmission device to be flexible in at least one direction that is perpendicular to the force transmission direction. In this way, adaptation of the shape of the force transmission device to the shape of the guide device can be effected especially when the guide device is not in the form of a linear guide device for guiding the force transmission device along a straight line.

Preferably, the force transmission device at least partly fills a cavity formed in the guide device, and in particular, fills it substantially entirely. Particularly reliable guidance of the force transmission device on the guide device is ensured in this way. Furthermore, it is thereby possible for force to be transmitted directly to the at least two tool elements of the surgical instrument since the force transmission device cannot deform within the guide device.

It is expedient for the surgical instrument to comprise a handle which can be gripped in a particularly easy manner by a surgeon for the purposes of manipulating the surgical instrument. The handle is preferably arranged on the guide device in non-rotatable manner. However, as an alternative or in addition thereto, provision could also be made for the handle to be arranged on the force transmission device in non-rotatable manner. The essential thing here is that either the guide device or the force transmission device is arranged such as to be non-rotatable relative to the handle. Particularly easy actuation of the coupling device can then be effected by rotating the respective other element relative to the handle.

It is particularly expedient if the surgical instrument comprises an actuating device for changing a coupling position of the coupling device, and in particular, for rotating the guide device relative to the handle. In this way, particularly simple actuation of the coupling device is possible and furthermore, it is possible for the handle of the surgical instrument to be of particularly simple construction. The actuating device is preferably arranged at a proximal end of the guide device which faces the handle.

It is expedient if the guide device is of rigid construction. In this way, particularly stable guidance of the force transmission device on the guide device is possible.

Furthermore, the guide device is preferably at least approximately in the form of a hollow cylinder, and in particular, is preferably in the form of an elongated shaft. In this way, even those locations in the body that are difficult to access can be reached by means of the surgical instrument.

It can be advantageous, if the guide device is at least partly electrically conductive. In this way, an electric current can be conveyed to at least one tool element of the surgical instrument by means of the guide device in a particularly simple manner. In particular, provision may be made for the guide device to be in the form of a first current supply line and for the force transmission device to be in the form of a second current supply line for the purposes of supplying the at least two tool elements of the surgical instrument with current.

The guide device and the force transmission device are preferably electrically insulated from each other.

The force transmission device can preferably be selectively coupled exclusively to a first tool element or to a second tool element. In this way, one can prevent the at least two tool elements of the surgical instrument that are movable relative to each other from being actuated simultaneously by the application of an actuating force to the force transmission device.

It is expedient, if the coupling device is arranged on the guide device in substantially non-rotatable manner. In this way, a change in the coupling position of the force transmission device can be effected in a particularly simple manner by rotating the force transmission device relative to the guide device or by rotating the guide device relative to the force transmission device.

In one embodiment of the invention, provision may be made for the surgical instrument to comprise an electrical switching device for selectively applying electrical energy to at least one of the at least two tool elements. To this end for example, at least one of the at least two tool elements is moveable into direct or indirect electrically conductive engagement with a terminal for the application of an electrical voltage by means of the switching device. In particular hereby, provision may be made for exclusively applying electrical energy on each occasion to just one of the at least two tool elements of the surgical instrument that are movable relative to one another.

For the purposes of transmitting electrical energy to the at least one of the at least two tool elements, the at least one of the at least two tool elements comprises at least one contact point for the direct transferral of electrical energy and/or at least one coupling point for the transferral of an alternating voltage to the at least one of the at least two tool elements in contact-free manner.

The electrical switching device is preferably arranged at the distal end of the guide device. An electric current can thus be fed from the proximal end of the guide device to the distal end of the guide device using just a single electrical line. Coupling of this one electrical line to the at least one of the at least two tool elements to which electrical energy is to be applied on each occasion then takes place only at the distal end of the guide device.

In one embodiment of the invention, provision is made for the coupling device to be electrically conductive at least in sections thereof for the purposes of conveying an electric current from the force transmission device to at least one of the at least two tool elements. The coupling device then preferably comprises the electrical switching device or forms the electrical switching device so that, particularly when switching-over the coupling point for the purposes of mechanically coupling the at least one tool element to the force transmission device, an electrical connection between the force transmission device and the coupled tool is established at the same time by means of the coupling device.

The coupling device is preferably formed for conveying an electric current from the force transmission device to the first tool element in a first coupling position of the force transmission device in which the force transmission device is coupled to a first tool element, and from the force transmission device to the second tool element in a second coupling position in which the force transmission device is coupled to a second tool element. Since the coupling device thus enables both a mechanical coupling and an electrical coupling of the force transmission device to at least one of the at least two tool elements, a separate electrical switching device can be dispensed with in this embodiment.

In one embodiment of the invention, provision is made for the coupling device to comprise at least one coupling member which is moveable into engagement with at least one coupling member of the force transmission device for producing a positive connection between the coupling device and the force transmission device in a force transmission direction of the force transmission device.

In this way, it is possible to produce a particularly stable connection between the force transmission device and the coupling device in the force transmission direction so that an actuating force is reliably transferable to at least one of the at least two tool elements of the surgical instrument by means of the force transmission device and the coupling device.

The at least one coupling member of the coupling device and the at least one coupling member of the force transmission device are preferably configured and arranged relative to each other in such a way that they are moveable into engagement and out of engagement with one another by rotating the at least one coupling member of the coupling device relative to the at least one coupling member of the force transmission device. In order to ensure particularly trouble-free and reliable manipulation of the surgical instrument, provision may be made for the coupling device to have at least one coupling aid in the form of a lead-in chamfer for example so as to simplify the coupling of the force transmission device to at least one of the at least two tool elements. To this end for example, provision may be made for at least one coupling member of the coupling device and/or at least one coupling member of the force transmission device to have a lead-in chamfer so that the at least one coupling member of the coupling device and the at least one coupling member of the force transmission device do not get hooked together and thus make the process of switching-over the coupling position more difficult in the course of a rotary movement of the at least one coupling member of the coupling device relative to the at least one coupling member of the force transmission device for example.

In one embodiment of the invention, provision may be made for the force transmission device to be capable of being coupled directly to at least one of the at least two tool elements. To this end, provision may be made for each of the at least two tool elements of the surgical instrument to comprise at least one coupling member of the coupling device, and preferably to be formed in one piece manner with at least one coupling member of the coupling device.

In a further embodiment of the invention, provision may be made for the coupling device to comprise at least one coupling element for coupling the force transmission device to at least one of the at least two tool elements. In this way, it is possible have an indirect coupling of the force transmission device to at least one of the at least two tool elements of the surgical instrument.

To this end, the at least one coupling element preferably acts at a distal end of the force transmission device.

In one embodiment of the invention, provision may be made for the coupling device to comprise at least one coupling element for each of the tool elements of the surgical instrument that are movable relative to the guide device.

It is expedient, if the coupling device comprises at least two coupling elements which are electrically insulated from one another. In this way, the at least two tool elements of the surgical instrument, which are adapted to be coupled to the force transmission device by means of a respective coupling element for example, can be supplied with current independently of each other.

At least one coupling element of the coupling device is preferably arranged at least partly within the guide device. Particularly in the case where a coupling member of the force transmission device and a coupling member of the at least one coupling element are disposed entirely within the guide device, contamination of the coupling members and the more difficult manipulation of the coupling device that is caused thereby are effectively prevented.

In one embodiment of the invention, provision may be made for at least two coupling elements to be distributed symmetrically about a central axis of the guide device.

Furthermore, provision may be made for at least two coupling elements to be arranged on mutually opposite sides of a longitudinal centre plane of the guide device.

At least one coupling element of the coupling device is preferably mounted on the guide device such as to be displaceable in a force transmission direction of the force transmission device. In this way, an actuating force which is being transferred to the at least one coupling element by means of the force transmission device and is effective in the force transmission direction can be transferred in a particularly simple manner to at least one of the at least two tool elements of the surgical instrument by means of the at least one coupling element. By virtue of a suitable coupling of the at least one coupling element to the respective at least one of the at least two tool elements, the movement of the at least one coupling element in the force transmission direction can then preferably be converted into a movement of the at least one of the at least two tool elements in the force transmission direction or into a rotary movement of the at least one of the at least two tool elements about an axis of rotation of the at least one of the at least two tool elements which is orientated transversely, preferably substantially perpendicularly with respect to the force transmission direction.

In one embodiment of the invention, provision may be made for the coupling device to comprise at least one guideway for guiding at least one movable tool element. In particular, a guiding element of the at least one movable tool element can thereby be moved along a predetermined path. The at least one movable tool element can, for example, be rotated about an axis of rotation by a suitable shape of the guideway and/or of the guiding element.

It is expedient, if the surgical instrument comprises at least one tool element which is fixed with respect to the guide device.

Preferably, at least one of the at least two tool elements that are movable relative to the guide device together with the at least one tool element that is fixed with respect to the guide device forms a tool of the surgical instrument, for example, a clamping tool and/or a cutting tool. Hereby, actuation of the tool, for example, the carrying out of a clamping process and/or a cutting process, is preferably effected by moving the at least one tool element that is movable relative to the guide device relative to the guide device and thus relative to the tool element that is fixed with respect to the guide device.

Expediently, provision may be made for a first tool element that is movable relative to the guide device together with a tool element that is fixed with respect to the guide device to form a first tool, and, for a second tool element that is movable relative to the guide device together with the same tool element that is fixed with respect to the guide device to form a second tool. Due to the dual function of the tool element that is fixed with respect to the guide device and serves as a tool element for the first tool on the one hand and as a tool element for the second tool on the other, it is possible for the surgical instrument to be of particularly simple construction. Furthermore, provision may be made, particularly in the case where a current is applied to at least one of the tools of the surgical instrument, for the tool element that is fixed with respect to the guide device to always be connected to an electrical lead for the supply of current so that, for the purposes of selectively applying current to the one or the other tool of the surgical instrument, one merely needs to switch between the processes of applying current to the one tool element that is movable relative to the guide device and applying current to the other tool element that is movable relative to the guide device.

It is expedient, if at least one of the at least two tool elements is pivotal with respect to the guide device.

In particular, provision may be made for a first tool element and a second tool element to be mounted on the guide device such that they are pivotal in mutually opposite directions.

A first axis, about which a first tool element is pivotally mounted on the guide device for example, is preferably different from a second axis about which a second tool element is pivotally mounted on the guide device for example.

A simple construction of the surgical instrument is then possible especially if the first axis is aligned parallel to the second axis.

In principle, provision may be made for the surgical instrument to be formed of an electrically insulating material so that current cannot be conveyed to the body of a person who is being operated on by means of the surgical instrument. However, in order to enable a current to be conveyed from the surgical instrument to specific parts of the body that are being operated on, provision may however be made for at least one of the at least two tool elements to be configured such as to be electrically conductive at least in sections thereof. In this way at least, an electric current can be conveyed to the part of the body that is being operated on directly at the point whereat the at least one of the at least two tool elements of the surgical instrument is acting.

In one embodiment of the invention, provision is made for the surgical instrument to comprise at least one insulating element for the purposes of electrically insulating the force transmission device, the guide device, at least one coupling element and/or at least one tool element. In particular, it is necessary in the case of bipolar application of current to a tool of the surgical instrument to electrically insulate from each other the two electrical leads that are necessary for this purpose and which are formed by the guide device and/or the force transmission device for example or which run along the guide device.

On the one hand, provision may be made for at least one insulating element to be in the form of a coating. As an alternative or in addition thereto, provision may be made for the at least one insulating element to be in the form of an additional component of the surgical instrument.

In particular, the at least one insulating element is formed from an electrically insulating material and in particular from a ceramic material.

In the surgical instrument according to the invention, the force transmission device can advantageously serve for both the processes of mechanically switching between at least two tool elements and electrically switching between at least two tool elements. Basically in this way, the at least two tool elements can be activated by electric current and thus operated in bipolar manner. At least two current conveying means for the at least two tool elements and a mutual insulating means therefor are preferably replaced by just a single element, namely, the force transmission device. In consequence, this force transmission device can be of more substantial construction so as to obtain greater stability of the surgical instrument when in operation, and hence lesser resilient deformation and greater tactility.

The construction of the handle of the surgical instrument is preferably simplified thereby. This enables the handle to be of lighter and slimmer design.

Furthermore, provision can be made in the surgical instrument according to the invention for the possibility of more accurate switching between the coupling positions of the force transmission device as a result of the smaller differences in tolerance and the smaller amount of resilient deformation in the switching range that are obtained by the use of just a single force transmission device.

In particular, in order to prevent unwanted actuation of the at least one of the at least two tool elements that is not actually coupled to the force transmission device, provision may be made for the surgical instrument to comprise a latching device for latching the at least one tool element that is not in current use.

Preferably, the latching device for latching the at least one tool element that is not in current use comprises at least one blocking element for blocking a movement and in particular a movement in the force transmission direction of the at least one tool element that is not coupled to the force transmission device.

It is expedient, if the at least one blocking element is arranged in the vicinity of the distal end of the force transmission device. Preferably, the blocking element is held on the instrument in movable manner.

In particular, provision may be made for the at least one blocking element to cooperate with the force transmission device in the vicinity of the distal end of the force transmission device. Preferably, the blocking element is held in such a manner that it will automatically be moved along therewith as a result of a movement of the force transmission device. For example, the force transmission device can be configured at least in part as a driver which rests against the blocking element and forces the blocking element to move as the result of a rotation of the force transmission device about a longitudinal axis of the guide device for example.

Furthermore, provision may be made for the at least one blocking element to be arranged in the vicinity of the distal end of the guide device.

The at least one blocking element is preferably held on the guide device in guided movable manner. For example, a tongue and groove guide means that is formed partially on the guide device and partially on the blocking element may be provided in order to guide a movement of the blocking element and the guide device relative to each other.

Preferably, the at least one blocking element is rotatable about an axis of rotation, and in particular about a rotational axis of the guide device in the vicinity of the distal end of the guide device, for example, about the central axis of the guide device.

In order to prevent unwanted electrical contacts in particular, provision may be made for the at least one blocking element to have an at least partially non-conductive surface. Preferably, the entire surface of the blocking element is non-conductive, i.e. it is formed in electrically insulating manner, for example, by the provision of an insulating coating. Furthermore, provision may be made for the at least one blocking element to be formed at least partially, and preferably completely, from a non-conductive, i.e. an electrically insulating material, for example, from a ceramic material or a synthetic material.

It is particularly expedient, if the at least one blocking element is operable by means of an actuating device, for example, by means of the actuating device for changing a coupling position of the coupling device. Hereby, the at least one blocking element is preferably moveable from a first blocking position in which the movement of the first movable tool element is blocked, into a second blocking position in which the movement of the second movable tool element is blocked.

It is expedient, if the at least one blocking element cooperates with the force transmission device in such a way that, in the course of a rotation of the force transmission device relative to the movable tool elements for the purposes of changing the coupling position, there is a simultaneous rotation of the at least one blocking element in order to move the at least one blocking element from a first blocking position into a further blocking position, for example, from the first blocking position into the second blocking position.

Preferably, at least one movable tool element is blockable in a closed position by means of the at least one blocking element.

As an alternative thereto however, provision could also be made for at least one tool element to be blockable in an open position by means of the at least one blocking element.

In particular, the use of at least one blocking element for blocking a movement of at least one tool element that is not coupled to the force transmission device can have the advantage that an unwanted actuation of the tool element that is not coupled to the force transmission device is prevented when using the surgical instrument. Consequently, particularly safe handling of the surgical instrument is possible.

Similar or functionally equivalent features are provided with the same reference symbols in each of the Figures.

A surgical instrument 100 that is illustrated exemplarily in FIGS. 1 to 11 comprises a handle 102, a guide device 104, a first tool 106 and a second tool 108.

The handle 102 comprises a fixed branch 110 with a finger opening 112 and a movable branch 114 with a finger opening 116. A surgeon for example can grip the handle 102 and actuate the first tool 106 or the second tool 108 by a relative movement between the movable branch 114 and the fixed branch 110.

Furthermore, for the purposes of applying a voltage, the handle 102 comprises terminals 118 which can be connected to the first tool 106 and/or the second tool 108 by means of electrical leads.

The guide device 104 is configured to be substantially rotationally symmetrical about a central axis 117 of the guide device 104 and it comprises a cylindrical cavity 119. The guide device 104 is thus in the form of an elongated shaft.

The handle 102 is connected to the guide device 104 and to a force transmission device 120 which is guided in the cylindrical cavity 119 of the guide device 104, this thereby ensuring a movement relative to the guide device 104 in a force transmission direction 122 of the force transmission device 120 and/or a rotational movement of the force transmission device 120 relative to the guide device 104.

Provision is made in particular, for the force transmission device 120 to be arranged on the handle 102 in non-rotatable manner and for the guide device 104 to be mounted on the handle 102 such that it is rotatable about an axis running in parallel with the force transmission direction 122.

For the purposes of rotating the guide device 104 about the axis that is aligned in parallel with the force transmission direction 122, there is provided at a proximal end 124 of the guide device 104 facing the handle 102 an actuating device 128 which is in the form of a rotary element 126 for example. A surgeon who is utilising the surgical instrument 100 can rotate the guide device 104 about the axis that is aligned in parallel with the force transmission direction 122 in a particularly simple manner by means of the actuating device 128. The first tool 106 and the second tool 108 are arranged at a distal end 130 of the guide device 104 which is remote from the handle 102.

As can be perceived in particular from FIG. 2, the surgical instrument 100 comprises a tool element 132 which is fixed with respect to the guide device 104, a first movable tool element 134 which is pivotally mounted on the guide device 104 and a second movable tool element 136 which is pivotally mounted on the guide device 104. The fixed tool element 132 together with the first movable tool element 134 form the first tool 106. Furthermore, the fixed tool element 132 together with the second movable tool element 136 form the second tool 108.

The first movable tool element 134 is mounted on the guide device 104 such as to be pivotal about a first axis 138, wherein the first axis 138 is oriented perpendicularly with respect to the force transmission direction 122.

The second movable tool element 136 is mounted on the guide device 104 such as to be pivotal about a second axis 140 (see FIG. 5), wherein the second axis 140 is likewise oriented perpendicularly with respect to the force transmission direction 122, but does not however coincide with the first axis 138. The first axis 138 and the second axis 140 are however preferably aligned in parallel with each other.

Furthermore, the surgical instrument 100 comprises a coupling device 142 for selectively coupling the force transmission device 120 to the first movable tool element 134 or to the second movable tool element 136. To this end, the coupling device 142 comprises two coupling elements, namely, a first coupling element 144 which is associated with the first movable tool element 134 and a second coupling element 146 which is associated with the second movable tool element 136. The coupling elements 144, 146 are arranged on mutually opposite sides of a longitudinal centre plane 147 of the guide device 104 which runs through the central axis 117 of the guide device 104.

As can be perceived in particular from FIG. 5, the force transmission device 120 comprises, at a distal end 148 of the force transmission device 120, a coupling member 150 which can be positively connected in the force transmission direction 122 to a coupling member 152 of the first coupling element 144 that is associated with the first movable tool element 134.

In a closed position of the first movable tool element 134 and the second movable tool element 136 which is illustrated in FIG. 5 for example, the coupling member 152 of the first coupling element 144 that is associated with the first movable tool element 134 is arranged opposite a coupling member 154 of the second coupling element 146 that is associated with the second movable tool element 136. This coupling member 154 of the second coupling element 146 that is associated with the second movable tool element 136 is also configured in such a way that it can be positively connected in the force transmission direction 122 to the coupling member 150 of the force transmission device 120.

The coupling device 142 comprises at least one coupling aid 153 in the form of a lead-in chamfer for example for the purposes of simplifying the coupling process for the coupling members 150, 152, 154.

In the coupling position illustrated in FIG. 5, i.e. in an arrangement of the force transmission device 120 and the coupling device 142 which is such that the coupling member 150 of the force transmission device 120 is in engagement with the coupling member 152 of the first coupling element 144 that is associated with the first movable tool element 134, a force can be transferred to the first movable tool element 134 by means of the force transmission device 120 since the first coupling element 144 passes on the force that has been transferred thereto to the first movable tool element 134.

For this purpose as can be perceived from FIG. 4, the first coupling element 144 comprises a guideway 156 in which a guide pin 158 of the first movable tool element 134 engages. Due to a movement of the first coupling element 144 by means of the force transmission device 120, the guide pin 158 of the first movable tool element 134 is shifted along the guideway 156 so that the first movable tool element 134 is pivoted about the first axis 138. The movement of the force transmission device 120 in the force transmission direction 122 is thus converted by means of the first coupling element 144 into a pivotal movement of the first movable tool element 134.

The coupling device 142 and the tools 106, 108 are arranged on the guide device 104 such as to be non-rotatable with respect to an axis running parallel to the force transmission direction 122 so that, in the course of a rotation of the force transmission device 120 relative to the guide device 104 about an axis parallel to the force transmission direction 122, a rotary movement of the force transmission device 120 relative to the coupling device 142 will also occur.

For this purpose as already explained, the force transmission device 120 can be rotated relative to the handle 102 if the guide device 104 is connected to the handle 102 in mutually non-rotatable manner. As an alternative thereto however, the guide device 104 together with the coupling device 142 and the tools 106, 108 could also be rotated if the force transmission device 120 is arranged on the handle 102 in mutually non-rotatable manner. By rotating the force transmission device 120 relative to the coupling device 142, the coupling member 150 of the force transmission device 120 can be disengaged from the coupling member 152 of the first coupling element 144 that is associated with the first movable tool element 134 and brought into engagement with the coupling member 154 of the second coupling element 146 that is associated with the second movable tool element 136.

In this way, the force transmission device 120 can be selectively coupled to the first coupling element 144 and thus to the first movable tool element 134 or to the second coupling element 146 and thus to the second movable tool element 136.

The second coupling element 146 comprises a guideway 160 in which a guide pin 162 of the second movable tool element 136 is guided. In correspondence with the functioning of the first coupling element 144 and the first movable tool element 134, a movement in the force transmission direction 122 that is transferred by means of the second coupling element 146 from the force transmission device 120 to the second coupling element 146 can be converted into a pivotal movement of the second movable tool element 136 by means of the guideway 160 and the guide pin 162.

The first movable tool element 134 and the second movable tool element 136 preferably act on mutually opposite sides of the tool element 132 that is fixed with respect to the guide device 104.

The upper surface 164 of the fixed tool element 132 facing the first movable tool element 134 and the lower surface 166 of the first movable tool element 134 facing the fixed tool element 132 comprise pointed projections 168 which enable an object clamped between the first movable tool element 134 and the fixed tool element 132 to be firmly clamped in a particularly secure manner (see FIG. 4).

The tool 106 formed by the first movable tool element 134 and the fixed tool element 132 is thus in the form of a clamping tool.

The lower surface 170 of the fixed tool element 132 remote from the upper surface 164 of the fixed tool element 132 is in the form of a cutting edge 172 which cooperates with the second movable tool element 136 that is in the form of a cutting blade 174 so that the second tool 108 formed by the second movable tool element 136 and the fixed tool element 132 is in the form of a cutting tool (see FIG. 9).

The surgical instrument 100 is thus selectively usable as a clamping tool or as a cutting tool. Furthermore, in addition to the clamping function and the cutting function of the surgical instrument 100, a current can be conveyed to an object being worked upon by means of the surgical instrument 100. To this end, bipolar current can preferably be applied to the movable tool elements 134, 136 on the one hand and to the fixed tool element 132 on the other.

In the embodiment of a surgical instrument 100 illustrated in FIGS. 1 to 11 however, no provision is made for the application of current to the second movable tool element 136. Rathermore, it is only the first movable tool element 134 together with the fixed tool element 132 to which a current can be applied.

To this end, the guide device 104 and the force transmission device 120 are formed such as to be at least partly electrically conductive, wherein the guide device 104 and the force transmission device 120 are electrically insulated from each other. For the purposes of conveying a bipolar current to the first tool 106, the connection between the fixed tool element 132 and the guide device 104 is electrically conductive. The guide device 104 is in turn connected electrically to one of the terminals 118. The other one of the terminals 118 is connected electrically to the force transmission device 120 which is moveable into engagement with the electrically conductive first coupling element 144 at the distal end 148 thereof. Since the connection between the first coupling element 144 and the force transmission device 120 and the connection between the first coupling element 144 and the first movable tool element 134 enable an electric current to be conveyed, a current can be conveyed from the force transmission device 120 to the first movable tool element 134. In order to prevent a short-circuit between the force transmission device 120, the first coupling element 144 and the first movable tool element 134 on the one hand and the guide device 104 and the tool element 132 that is fixed with respect to the guide device 104, there are provided two insulating elements 176 at the distal end 130 of the guide device 104, said insulating elements spatially separating the first coupling element 144 and the first movable tool element 134 from the guide device 104 and the fixed tool element 132 and being formed of an electrically insulating material.

Basically, the coupling device 142 also serves as an electrical switching device 178, with the aid of which current can be selectively switched between the first movable tool element 134 or the second movable tool element 136.

In the embodiment illustrated in FIGS. 1 to 11 however, provision is only made for a current to be conveyable from the force transmission device 120 to the first coupling element 144 in order to prevent a short-circuit at the second movable tool element 136 which is not insulated with respect to the guide device 104. To this end for example, the coupling element 146 can be formed of an electrically insulating material or it can be provided with an electrically insulating coating.

As is perceivable in particular from FIG. 2, the surgical instrument 100 comprises a blocking element 180 which is guided on the inner surface of the guide device 104 by means of a partially annular projection 182 of the blocking element 180. To this end, the guide device 104 incorporates an annular groove 184 into which the projection 182 of the blocking element 180 extends.

The groove 184 in the guide device 104 runs in a plane which is perpendicular to the force transmission direction 122 of the force transmission device 120 so that the blocking element 180 cannot be displaced in the force transmission direction 122 but can however be rotated about the central axis 117.

The groove 184 in the guide device 104 is formed by means of two annular projections 186 of the guide device 104. In a not illustrated further embodiment however, the groove 184 could also be formed merely by means of an annular recess in a wall of the guide device 104 for example.

In the assembled state of the surgical instrument 100, the blocking element 180 abuts against the force transmission device 120 and is rotatable about the central axis 117 of the guide device 104 by means of a rotation of the force transmission device 120. Thereby, the blocking element 180 can be moved from a position in which the force transmission device 120 is coupled to the first movable tool element 134 for example and the blocking element 180 blocks a movement of the second movable tool element 136, into a position in which the force transmission device 120 is coupled to the second movable tool element 136 and the blocking device 180 blocks a movement of the first movable tool element 134.

For the purposes of electrically insulating it from the adjacent components of the surgical instrument 100, provision may be made for the blocking element 180 to have an electrically non conductive surface at least in the region thereof where it comes into contact with the guide device 104 and/or with the force transmission device 120. Furthermore, provision may be made for the blocking element 180 to be formed, in particular entirely, from an electrically insulating material, for example, from a ceramic material.

The previously described surgical instrument 100 is preferably used as follows:

In a preparatory phase, an electrical voltage is connected to the terminals 118 so that the first tool 106 can be supplied with bipolar current.

The actual use of the surgical instrument 100 is usually effected by a surgeon who grips hold of the handle 102 and rotates the guide device 104 including the coupling device 142 and the tools 106, 108 relative to the force transmission device 120 by manipulating the actuating device 128 in order to prepare the surgical instrument 100 for the actuation of the desired tool 106, 108.

By rotating the guide device 104 relative to the force transmission device 120, the force transmission device 120 is selectively coupled to the first movable tool element 134 or to the second movable tool element 136. To this end in particular, the coupling member 150 of the force transmission device 120 is selectively brought into engagement with the coupling member 152 of the first coupling element 144 that is associated with the first movable tool element 134 or with the coupling member 154 of the second coupling element 146 that is associated with the second movable tool element 136. The tool element 134, 136 which is not coupled to the force transmission device 120 on this occasion is preferably held or blocked in the closed position by means of the blocking element 180 so as to prevent an unwanted movement of the tool element 134, 136 that is not coupled to the force transmission device 120. By a movement of the movable branch 114 of the handle 102 relative to the fixed branch 110 of the handle 102, the force transmission device 120 is shifted along the guide device 104 in the force transmission direction 122 and an actuating force is thereby transferred from the proximal end 124 of the guide device 104 to the distal end 130 of the guide device 104. The movement of the force transmission device 120 in the force transmission direction 122 is transferred by means of the coupling element coupled to the force transmission device 120, i.e. either the first coupling element 144 or the second coupling element 146, to the movable tool element that is to be moved, i.e. either to the first movable tool element 134 or to the second movable tool element 136, whereby the movement of the force transmission device 120 in the force transmission direction 122 is converted by means of the first coupling element 144 or by means of the second coupling element 146 into a pivotal movement of the first movable tool element 134 or a pivotal movement of the second movable tool element 136. Due to the movement of the first movable tool element 134, the first tool 106 can be brought into an open position (see FIG. 4) in which an object that is to be gripped by means of the first tool 106 can be inserted between the first movable tool element 134 and the fixed tool element 132. For example, an artery can be grasped in this way by means of the first tool 106. The artery can then be welded by means of the bipolar current which is conveyable to the first tool 106 and is preferably a high frequency (HF) current.

After the opening of the first tool 106 and removal of the artery from the first tool 106, the first tool 106 is again closed so that, in a next step, the force transmission device 120 can be rotated again relative to the guide device 104 by a renewed manipulation of the actuating device 128 in order to bring the coupling member 150 of the force transmission device 120 into engagement with the coupling member 154 of the second coupling element 146 that is associated with the second movable tool element 136.

By displacing the force transmission device 120 relative to the guide device 104 in the force transmission direction 122 by means of a movement of the movable branch 114 relative to the fixed branch 110 of the handle 102, the second tool 108 can be brought into an open position, i.e. the second movable tool element 136 can be pivoted away from the fixed tool element 132 so that, for example, the previously worked artery can be inserted between the cutting edge 172 on the lower surface 170 of the fixed tool element 132 and the second movable tool element 136 that is in the form of a knife blade 174. By withdrawing the force transmission device 120 relative to the guide device 104 in a direction opposed to the force transmission direction 122, the second tool 108 is closed; the second movable tool element 136 in the form of a knife blade 174 thereby moves towards the cutting edge 172 on the lower surface 170 of the fixed tool element 132 and severs the artery arranged between them.

Due to the fact that the surgical instrument 100 comprises a coupling device 142 for selectively coupling the force transmission device 120 directly or indirectly to at least one of the at least two tool elements 134, 136, the actuating force being exerted by the surgeon can be transferred particularly directly and without resilient deformation of the guide device 104 and/or the force transmission device 120 from the proximal end 124 of the guide device 104 to the distal end 130 of the guide device 104. The surgeon therefore has particularly advantageous tactile feedback from the tools 106, 108.

What is claimed is:

1. Surgical instrument, comprising:
   at least two tool elements that are movable relative to one another,
   a guide device,
   a force transmission device consisting of a single force transmission member,
   and a coupling device,
   wherein:
      the at least two tool elements are arranged at a distal end of the guide device,
      the at least two tool elements comprise at least a first tool element and a second tool element,
      the force transmission device is arranged to be selectively coupled exclusively to the first tool element or to the second tool element,
      the force transmission device is configured for transferring an actuating force from a proximal end of the force transmission device to a distal end of the force transmission device for moving the first tool element or the second tool element relative to the guide device,
      the coupling device is configured for a selective coupling and uncoupling of the distal end of the force transmission device directly or indirectly to the first tool element or to the second tool element, and
      the force transmission device is moveable from a first coupling position in which the force transmission device is exclusively coupled to the first tool element, into a second coupling position in which the force transmission device is exclusively coupled to the second tool element.

2. Surgical instrument according to claim 1, wherein the force transmission device is mounted within the guide device in a rotatable manner.

3. Surgical instrument according to claim 1, further comprising:
   a handle on which the guide device is arranged in a non-rotatable manner.

4. Surgical instrument according to claim 1, further comprising:
   a handle on which the force transmission device is arranged in a non-rotatable manner.

5. Surgical instrument according to claim 1, further comprising:
   an actuating device for changing a coupling position of the coupling device.

6. Surgical instrument according to claim 1, wherein the guide device is at least partially electrically conductive.

7. Surgical instrument according to claim 1, wherein the coupling device is arranged within the guide device in a substantially non-rotatable manner.

8. Surgical instrument according to claim 1, further comprising:
   an electrical switching device for selectively applying electrical energy to at least one of the first tool element or the second tool element.

9. Surgical instrument according to claim 8, wherein the coupling device comprises the electrical switching device.

10. Surgical instrument according to claim 1, wherein the coupling device is electrically conductive at least in sections thereof for conveying an electric current from the force transmission device to at least one of the first tool element or the second tool element.

11. Surgical instrument according to claim 10, wherein the coupling device is configured for the conveying of the electric current from the force transmission device to the first tool element in a first coupling position of the force transmission device in which the force transmission device is coupled to the first tool element, and from the force transmission device to the second tool element in a second coupling position in which the force transmission device is coupled to the second tool element.

12. Surgical instrument according to claim 1, wherein the coupling device comprises at least one coupling member which is moveable into engagement with at least one corresponding coupling member of the force transmission device for producing a positive connection between the coupling device and the force transmission device in a force transmission direction of the force transmission device.

13. Surgical instrument according to claim 1, wherein the coupling device has at least one coupling aid for simplifying the coupling of the force transmission device to the first tool element or to the second tool element.

14. Surgical instrument according to claim 1, wherein the coupling device comprises at least one coupling element for coupling the force transmission device to the first tool element or to the second tool element.

15. Surgical instrument according to claim 14, wherein one of the at least one coupling element is provided for each of the first tool element and the second tool element.

16. Surgical instrument according to claim 14, wherein the at least one coupling element is mounted so as to be displaceable in a force transmission direction of the force transmission device.

17. Surgical instrument according to claim 1, wherein the coupling device comprises at least one guideway for guiding at least one of the first tool element or the second tool element.

18. Surgical instrument according to claim 1, wherein at least one of the first tool element or the second tool element is fixed with respect to the guide device.

19. Surgical instrument according to claim 1, further comprising:
   at least one insulating element for electrically insulating at least one of the force transmission device, the guide device, at least one coupling element, and at least one of the first tool element or the second tool element.

20. Surgical instrument according to claim 1, further comprising:
a latching device for latching one of the first tool element or the second tool element that is not currently being used.

21. Surgical instrument according to claim 20, wherein the latching device comprises a blocking element for blocking a movement of the one of the first tool element or the second tool element that is not coupled to the force transmission device.

22. Surgical instrument according to claim 21, wherein the blocking element is held movably on the instrument in a vicinity of the distal end of the force transmission device.

23. Surgical instrument according to claim 21, wherein the blocking element is moveable by means of an actuating device from a first blocking position in which a movement of the first tool element is blocked, into a second blocking position in which a movement of the second tool element is blocked.

* * * * *